(12) United States Patent
Murillo Gutierrez

(10) Patent No.: US 8,802,915 B2
(45) Date of Patent: Aug. 12, 2014

(54) HYDROCARBON DECOMPOSITION FOR SOIL AND WATER REMEDIATION

(71) Applicant: Pedro Murillo Gutierrez, Chihuahua (MX)

(72) Inventor: Pedro Murillo Gutierrez, Chihuahua (MX)

( * ) Notice: Subject to any disclaimer, the term of this patent is extended or adjusted under 35 U.S.C. 154(b) by 0 days.

(21) Appl. No.: 13/793,119

(22) Filed: Mar. 11, 2013

(65) Prior Publication Data

US 2013/0187081 A1 Jul. 25, 2013

Related U.S. Application Data

(60) Division of application No. 12/768,234, filed on Apr. 27, 2010, now Pat. No. 8,415,522, which is a continuation of application No. PCT/MX2009/000065, filed on Jul. 13, 2009.

(30) Foreign Application Priority Data

Jul. 3, 2009 (MX) .................... MX/a/2009/007423

(51) Int. Cl.
*A62D 3/36* (2007.01)

(52) U.S. Cl.
USPC .......................................... 588/318; 588/405

(58) Field of Classification Search
USPC ........................ 423/245.1; 588/313, 318, 405
See application file for complete search history.

(56) References Cited

U.S. PATENT DOCUMENTS

| | | | |
|---|---|---|---|
| 4,612,190 | A | 9/1986 | Sato et al. |
| 4,666,677 | A | 5/1987 | Ramus et al. |
| 5,250,197 | A | 10/1993 | Marcel |
| 5,252,138 | A | 10/1993 | Guymon |
| 5,472,638 | A | 12/1995 | McLaughlin et al. |
| 5,671,762 | A | 9/1997 | Hancock, Jr. et al. |

OTHER PUBLICATIONS

"Extraction and Purification of Nordihydroguaiaretic acid"; by J. O. Page; 23 Anal. Chem; 1951; pp. 296-298.

*Primary Examiner* — Edward Johnson
(74) *Attorney, Agent, or Firm* — St. Onge Steward Johnston & Reens LLC

(57) ABSTRACT

Presented herein are compositions including a linear tenso-active surfactant which, upon contact and mechanical stirring of a hydrocarbon body, induces emulsification, resulting in oxidation of fatty acid aliphatic bodies. The compositions solve the problem of hydrocarbon pollution. The hydrocarbon decomposer and its by-products dissolve hydrocarbons present in polluted bodies such as clays, soils, water and sand. Methods of the invention create a residue that is a fertilizer, at room temperature and with no need for high pressure.

6 Claims, No Drawings

HYDROCARBON DECOMPOSITION FOR SOIL AND WATER REMEDIATION

FIELD OF THE INVENTION

The present invention provides a novel process for the reduction of hydrocarbon pollution from environmental sites. More specifically, this invention provides compositions derived from dihydroguaiaretic acid, their methods of use for elimination of hydrocarbon pollution by reduction and oxidation of hydrocarbon bodies to produce naturally occurring soil components.

BACKGROUND OF THE INVENTION

Today, there are a number of methods and practices that offer to bio-remediate hydrocarbon-polluted sites and bodies. However, these methods typically only remove the polluting agent and move it to a different location.

Until now, the closest technique to this invention was based on sequestrants, flocculants, surfactants, etc., which extract the hydrocarbon-polluted bodies. However, these methods only move pollution to confinement sites and do not actually eliminate it.

For example, U.S. Pat. No. 5,252,138 to Guymon describes a water/surfactant process for removing oil from a soil that has been contaminated by an oil spill. The process disclosed aims to overcome a problem of many prior methods, emulsion of the hydrocarbons with the wash water. The surfactant is selected from the group consisting of linear alcohols having eight to fifteen carbon atoms and two to eight ethylene oxide units on the carbon atoms. The amount of surfactant must be carefully monitored so as not to exceed 0.5% or an emulsion forms. However, the oil removed from the process is still present in a vessel and must be disposed of.

Standards require that a bio-recovered site should be able to sustain natural biodiversity. Therefore, a scientific model has been created to solve the problem at its root cause and all its consequences. In view of the foregoing, what is desired is simple process for removing hydrocarbon pollution in which the hydrocarbons are eliminated rather than relocated to a confinement site.

SUMMARY OF THE INVENTION

Presented herein are processes of treating hydrocarbon polluted sites comprising use of a linear tenso-active surfactant which, upon contact and mechanical stirring of a hydrocarbon contaminated body, induces emulsification, resulting in oxidation of the hydrocarbons. The process solves the problem of hydrocarbon pollution by dissolving and releasing hydrocarbons present in polluted bodies such as clays, soils, water, sand leaving various mineral agents. Methods of the invention can be effected at room temperature and without high pressures, and the end product residue can enhance plant growth.

As a result of investigations searching for an agent to reduce hydrocarbon pollution, it has been found that compositions comprising dihydroguaiaretic acid and a phosphate source cause unlinking of the structural chain that characterizes the hydrocarbon, leaving the site with end products that that can serve as building blocks for soil nutrients. Residues do not need to be confined, but rather may remain in situ, as this promotes a faster recovery of the damaged soil.

Accordingly, an object of this invention is to provide a process for reducing hydrocarbon pollution of contaminated sites by using a dihydroguaiaretic derived surfactant that releases the hydrocarbon polluted bodies and their by-products leaving mineral agents.

Another object of the invention is to provide compositions comprising dihydroguaiaretic acid for use in reduction of hydrocarbon pollution.

Another object of the present invention is to provide methods for aliphatic body oxidation comprising dihydroguaiaretic acid that unlink and dissolve hydrocarbon chains.

A further object of the invention is to provide a method of converting hydrocarbon pollution in polluted sites to harmless mineral agents which may remain in situ.

Yet another object of the invention is to create a residue, at room temperature and with no need for high pressure, from remediated hydrocarbon pollution that may be used as fertilizer.

These and other objects and features of this invention will become more readily apparent from the following description in which preferred or other embodiments of the invention have been set forth.

DETAILED DESCRIPTION OF THE INVENTION

Molecular structural bonds retain the elements of a molecule together. When these bonds are broken, the molecule breaks down into its constituent compounds and elements. In the present invention, the breaking of the hydrocarbon chains releases gases and aromatic bodies; light hydrocarbons can be evaporated, medium and heavy hydrocarbons will be oxidized and reduced and elemental metals can be used as fertilizer.

The present invention complies with bio-remediation standards and solves problems of decontamination, since processes and methods of the present invention oxidize and reduce the polluting agent at its molecular structure and transform it into biologically acceptable end products. The resulting components: nitrogen, oxygen, carbon, phosphorus, sulfur, copper, magnesium, manganese, etc., make it a high-impact fertilizer, and meet current standards for soil and water remediation. Previously polluted bodies, after treatment with the method, should be able to sustain biodiversity.

Compositions comprising dihydroguaiaretic acid and a phosphate source cause unlinking of the structural chain that characterizes the hydrocarbon, leaving the site with various mineral agents that have been determined to be the basis for natural soil nutrients. In the present invention, residues do not need to be confined, but rather may remain in situ, as this promotes a faster recovery of the damaged soil. This is a significant difference between current techniques and the present invention.

Compositions and methods of the invention utilize dihydroguaiaretic acid (DGA), represented by the structural formula:

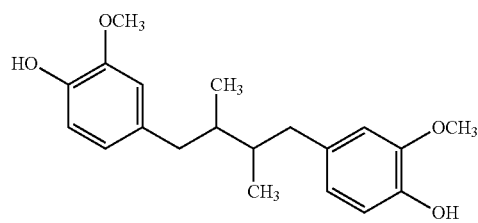 [SMILES: COc1cc(CC(C)C(C)Cc2ccc(O)c(OC)c2)ccc1O]

DGA is a lignin that may be extracted from plants such as *Larrea divaricata*. (See e.g. "Extraction and Purification of Nordihydroguaiaretic acid" by J. O. Page, 23 Anal. Chem. 1951 at 296-298.) *Larrea* is a genus of five species of New World evergreen shrubs that includes the cresosote bush. This tall, thorny shrub is found in large numbers in the deserts bordering the US and Mexico. For hundreds of years, Native American healers made a tea with the leaves and stems and used as a treatment for colds, flu, diarrhea, arthritis, cancer, venereal disease, tuberculosis, bowel cramps, and rheumatism. Twentieth century herbalists thought of this herb as an antibiotic and used it as a treatment for intestinal parasites. Although known for these and many other uses, DGA has not been disclosed for use in remediation of polluted sites.

The source of DGA is not limited to Larrea and may also be obtained from, for example *Machilus edulis* K., *Guaiacum officinale* L., and *Schizandra chinensis* B. or *Myristica argentea* H. as described in U.S. Pat. No. 4,612,190 to Sato et al, incorporated herein by reference.

The surfactant used in the invention is produced by extracting concentrates of DGA from biological sources. The DGA source is mixed with water, about 2% to about 4% phosphates and about 2% to about 4% sea salt, and then brought to a boil. Preferably, 2% phosphate is used. More preferably, 2% potassium phosphate monobasic is used. In a preferred embodiment 2% sea salt is also used. The boiling process is continued until probiosis is induced. Continued heating is applied, actuating an enzymatic reaction which leads to creation of an oily compound, which in turn becomes a powder. The resulting surfactant powder is then mixed with water to provide a surfactant solution, used for soil and water treatments.

The strength of the surfactant solution is varied according to the pollutant to be tackled. In a preferred embodiment, the surfactant powder is present at about 3% by weight. The appropriate concentration will be selected based on the variation of electrolytic charges that can be induced, along with the amount of plant acids that dissolve the hydrocarbons.

Compositions of the present invention may be used to treat a variety of samples. The compositions and methods are useful on any type of hydrocarbon pollution. Particularly, clays, soils, water and sand have all been cleaned immediately, as shown in laboratory tests. The ratio of surfactant solution to polluted sample can be varied. In preferred embodiments, a 1:1, 1:2 or 1:3 ratio of the surfactant solution: polluted sample is used. Most preferably, a 1:2 ratio of the compositions of the surfactant solution:polluted sample is used.

The polluted sample is then mechanically stirred with the surfactant solution. It is recommended to homogenize the surfactant solution with the polluted sample. The homogenization time is dependent on the level of hydrocarbon present in the polluted sample that needs to be treated. After homogenization, the sample may sit undisturbed for 24 hours in order for the aliphatic body oxidation system to interact with the hydrocarbon pollution. Impurities will float to the surface. Optionally, the sample may be rinsed with water and left to sit until drying occurs.

While not wishing to be bound by any theory, it is proposed that the surfactant composition aggressively breaks hydrocarbon bonds. The compositions of the invention dissolve or break the chemical bonds and cause the components of the large hydrocarbon chain to separate into short aliphatic chains or elemental compounds.

The polarity of electric charges is changed by the compound of the invention, inhibiting and breaking hydrocarbon bonds and causing the components of the hydrocarbon chain to separate into individual chains as a result of such separation. In the absence of aromatics, the resulting hydrocarbon no longer has the chemical characterization that identified it, such as adherence, viscosity, combustibility, etc.

The reduction process that is immediately linked to the oxidation caused by this invention produces a mixture within the residual washing fluid of small individual chains comprising nitrogen, hydrogen, oxygen, phosphorus, sodium chloride, salts and other metals. Ehtyls, methyls, carbons, other components are also present. As such, the invention produces an excellent fertilizer recommended for recovering highly impoverished soils.

EXAMPLES

The following examples are explanative of the results of applying the system to oxidize aliphatic compounds.

Example 1

A sample of hydrocarbon-polluted soil (clay with gasoline, diesel and oil), provided a representative sample of the light, medium and heavy phase of hydrocarbons and was subjected to the following treatment:150 grams of the 3% surfactant solution was added to 300 grams of polluted soil in a 1:2 ratio.

The mixture was homogenized mechanically for 20 minutes and left undisturbed 24 hours in order for the aliphatic body oxidation system to chemically interact with the polluted soil sample.

Then, in order to extract hydrocarbons from the mixture, the mixture was rinsed with 5×450-ml portions of plain water and vigorous mechanical shaking until completely homogenized, and left undisturbed for 24 hours.

After rinsing, the solid phase (treated soil) was separated by filtering. Hydrocarbon content was assessed in the solid sample, and in the drained liquid to determine hydrocarbon analysis in the soil sample and in the liquid phase.

Analyses: A mass chromatography analysis (volatile fractions) for polyaromatic hydrocarbons (PAHs); gas chromatography analysis (light and medium fractions) for gasoline and diesel; a Sixhiet extraction analysis (heavy fraction) on oils.

A portion of the sample was evaluated separately to calculate the percentage of solids and dry fraction mass was used to calculate heavy fraction hydrocarbon concentration in the dry mass.

Interpretation of the Results

The untreated polluted soil sample was determined to have a high hydrocarbon concentration (light fraction +heavy fraction) of 227,024.81 mg/kg. In the treated soil samples, the concentration decreased significantly, and it is therefore inferred that a breakdown has taken place, as the analysis of the treated sample revealed that the heavy fraction hydrocarbon concentration was significantly reduced, approximately by 80%. The analysis also showed that the hydrocarbon content in the filtering liquid had a concentration of 2,728.72 mg/kg.

These results lead us to conclude that a significant part of the initial hydrocarbon concentration was transformed into a volatile compound chain which was then lost through natural evaporation.

Example 2

From Technical Report of the System to Oxidize Aliphatic Compounds with Residual Crude Oil in Palo Blanco, Veracruz, Mexico A sample was polluted with crude oil, had oily-looking leaves, was black in color and had a foul odor.

The sample was subjected to three washing treatments with the 3% surfactant solution (aliphatic body oxidation system), as described below:

1:1, 1:2 and 1:3 ratios. One part polluted sample and 1, 2 and 3 parts of the aliphatic body oxidation system.

Once the appropriate assays were completed, the vegetation was partially cleaned out and the odor was reduced, as the product solubilized the hydrocarbon.

The results of the washing (Table 1) were chemically analyzed and showed that the composition was satisfactory to decharacterize the hydrocarbon, as the only elements found were phosphorus, iron, zinc, calcium, sodium, among others, as shown in the results sheet.

TABLE 1

FTIR Analysis results
Analysis of soil by the Autonomous University of Chihuahua

| Residual Sand contaminated with: | | Ground contaminated with: | |
|---|---|---|---|
| Nutrients | BioGrass Extra | Nutrients | BioGrass Extra |
| NO3 | 13.15 | NO3 | 13.66 |
| P | 54.00 | P | 91.00 |
| Fe | 10.62 | Fe | 11.05 |
| Zn | 6.23 | Zn | 0.92 |
| Cu | 0.45 | Cu | 0.71 |
| Mn | 9.42 | Mn | 52.3 |
| PH Paste | 8.65 | PH Paste | 8.05 |
| C.E. Mmhos/cm | 6.45 | C.E. Mmhos/cm | 14.02 |

TABLE 1-continued

FTIR Analysis results
Analysis of soil by the Autonomous University of Chihuahua

| Residual Sand contaminated with: | | Ground contaminated with: | |
|---|---|---|---|
| Soluble Salt Meq/l | | Soluble Salt Meq/l | |
| Cationes | | Cationes | |
| Ca | 0.55 | Ca | 4.06 |
| Mg | 0.47 | Mg | 3.59 |
| Na | 2.22 | Na | 8.65 |
| K | 2.28 | K | 3.94 |
| Aniones | | Aniones | |
| CO3 | 1.8 | CO3 | 0.36 |
| HCO3 | 4.68 | HCO3 | 8.1 |
| Cl | 9.24 | Cl | 48.4 |
| SO4 | 10.20 | SO4 | 36.62 |

What is claimed is:

1. A composition for reducing hydrocarbon pollution in a contaminated sample comprising: a dihydroguaiaretic acid-derived surfactant.

2. The composition of claim 1 further comprising: a phosphate.

3. The composition of claim 2 further comprising: sea salt.

4. The composition of claim 3 wherein the phosphate is potassium phosphate monobasic.

5. The composition of claim 3 wherein the composition is an aqueous solution containing about 2% to about 4% by weight of phosphate and about 2% to about 4% by weight of sea salt.

6. The composition of claim 5 wherein the phosphate is about 2% by weight and the sea salt is about 2% by weight.

* * * * *